(12) United States Patent
Hashino et al.

(10) Patent No.: US 9,308,139 B2
(45) Date of Patent: *Apr. 12, 2016

(54) INDIVIDUALLY PACKAGED PRODUCT

(75) Inventors: Akira Hashino, Kagawa (JP); Yuki Noda, Kagawa (JP); Shinpei Komatsu, Kagawa (JP); Hideyuki Kinoshita, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/006,768

(22) PCT Filed: Mar. 13, 2012

(86) PCT No.: PCT/JP2012/056458
§ 371 (c)(1),
(2), (4) Date: Sep. 23, 2013

(87) PCT Pub. No.: WO2012/128130
PCT Pub. Date: Sep. 27, 2012

(65) Prior Publication Data
US 2014/0012219 A1  Jan. 9, 2014

(30) Foreign Application Priority Data

Mar. 22, 2011  (JP) ................................ 2011-063088

(51) Int. Cl.
*A61F 13/551* (2006.01)

(52) U.S. Cl.
CPC .................................. *A61F 13/5514* (2013.01)

(58) Field of Classification Search
CPC ............ A61F 13/5514; A61F 13/5513; A61F 13/55135; A61F 13/55145; A61F 2013/8497; B65D 85/16; A47K 10/16
USPC .................. 206/440, 438, 459.5; 604/385.02, 604/385.05
See application file for complete search history.

(56) References Cited

U.S. PATENT DOCUMENTS 6,520,330 B1 * 2/2003 Batra ............................ 206/494
8,231,590 B2 * 7/2012 Zander et al. ............ 604/385.01
(Continued)

FOREIGN PATENT DOCUMENTS

EP    2 623 077 A1   8/2013
JP      3021237 U   11/1995
(Continued)

OTHER PUBLICATIONS

International Search Report from corresponding PCT application No. PCT/JP2012/056458 dated Jun. 19, 2012 (4 pgs).
(Continued)

*Primary Examiner* — Steven A. Reynolds
(74) *Attorney, Agent, or Firm* — Brinks Gilson & Lione

(57) ABSTRACT

An individual packing product that makes it difficult to see an absorbent product disposed therein, not staining other individual packing products, and easy to put in a bag or pocket and carry. In the individual packing product, the absorbent product having an adhesive portion in a non-skin contact region is packed with a packing sheet. The absorbent product is fixed to the inner side of the packing sheet with the adhesive portion being disposed therebetween, the packing sheet is folded with the absorbent product being disposed therein, the packing sheet has a separable colored portion on the inner side thereof, and although the colored portion can be seen from the outside of the individual packing product, the absorbent product cannot be seen from the outside of the individual packing product.

20 Claims, 7 Drawing Sheets

(56) References Cited

U.S. PATENT DOCUMENTS

| | | | |
|---|---|---|---|
| 2004/0015145 A1* | 1/2004 | Miura et al. | 604/367 |
| 2005/0145523 A1 | 7/2005 | Zander et al. | |
| 2005/0154365 A1* | 7/2005 | Zander et al. | 604/385.04 |
| 2006/0025739 A1* | 2/2006 | DiPalma et al. | 604/385.02 |
| 2006/0137568 A1* | 6/2006 | MacDonald et al. | 106/31.13 |
| 2007/0179467 A1 | 8/2007 | Shimizu et al. | |
| 2008/0212903 A1* | 9/2008 | Germanow et al. | 383/42 |
| 2009/0105681 A1* | 4/2009 | Chicoine et al. | 604/385.02 |
| 2010/0286645 A1* | 11/2010 | MacDonald et al. | 604/385.02 |
| 2011/0028931 A1* | 2/2011 | Fung | 604/385.02 |
| 2011/0034897 A1* | 2/2011 | Nomoto et al. | 604/385.02 |
| 2011/0270208 A1* | 11/2011 | Miura et al. | 604/385.02 |
| 2012/0283680 A1* | 11/2012 | Zander et al. | 604/365 |
| 2012/0310201 A1* | 12/2012 | Oates | 604/385.02 |

FOREIGN PATENT DOCUMENTS

| | | |
|---|---|---|
| JP | H 08322882 A | 12/1996 |
| JP | 2003-199786 A | 7/2003 |
| JP | 3617552 | 11/2004 |
| JP | 2006-026080 A | 2/2006 |
| JP | 2006-223757 A | 8/2006 |
| JP | 2007-518481 A | 7/2007 |
| JP | 3166605 U | 2/2011 |
| WO | WO 2005/065605 | 7/2005 |

OTHER PUBLICATIONS

European extended Search Report from corresponding European application No. 12760136.7 dated Oct. 1, 2014 (6 pgs).

* cited by examiner ative Effects of Invention

INDIVIDUALLY PACKAGED PRODUCT

RELATED APPLICATION

This application is a 35 U.S.C. §371 national phase filing of International Patent Application No. PCT/JP2012/056458, filed Mar. 13, 2012, through which and to which priority is claimed under 35 U.S.C. §119 to Japanese Patent Application No. 2011-063088, filed Mar. 22, 2011.

TECHNICAL FIELD

The present disclosure relates to an individually packaged product wherein an absorbent article having an adhesive section on the non-skin-contacting surface thereof is wrapped with a packaging sheet.

BACKGROUND ART

Individually packaged products are known which have absorbent articles such as sanitary napkins, panty liners and paper diapers wrapped with individual packaging sheets. Individual packaging of the absorbent articles allows each of the absorbent articles to be conveniently and hygienically carried.

In the individually packaged product, it is usually the case that the absorbent article inside can be seen from the outside of the individually packaged product, or it is apparent that the absorbent article is individually packaged, and therefore in order to disguise its sanitary nature, the individually packaged product is usually further placed in a pouch and encased in a bag or the like.

Therefore, it is preferred for an absorbent article housed in an individually packaged product to not be recognizable at a glance.

Thinner individually packaged products have also been developed as such individually packaged products, and are commercially available as products that neatly fit in bags and pockets and can be easily carried around.

In such thin individually packaged products, the entire outer surface of the individually packaged product is sometimes coated with a colored material so that the housed absorbent article is not recognizable at a glance. However, when the outer surface of an individually packaged product is coated with a colored material, problems such as color transfer, where color shades of the colored material become transferred to adjacent objects, can occur due to abrasion in the manufacturing line during production, abrasion between individually packaged products during distribution or abrasion inside the bag after purchase.

PTLs 1 to 4 are examples of individually packaged products wherein sections other than the outer surface of the packaging sheet are colored. In PTLs 1 to 3 there are described individually packaged products of absorbent articles in which the release layers are colored, while PTL 4 describes an individually packaged product of an absorbent article in which a drawing design is printed on the back sheet.

CITATION LIST

Patent Literature

PTL 1 Japanese Unexamined Patent Publication No. 8-322882
PTL 2 Japanese Unexamined Patent Publication No. 2006-223757
PTL 3 Japanese Patent No. 3617552
PTL 4 Japanese Unexamined Patent Publication No. 2003-199786

SUMMARY OF INVENTION

Technical Problem

However, since the individually packaged products described in PTLs 1 to 4 are not colored to an extent that hides the absorbent article in the individually packaged product, the interior absorbent article can be seen through the outer surface of the individually packaged product, and it has been necessary to further place it in a pouch or house it in a bag or the like, in order to prevent it from being seen by other people.

It is therefore an object of the present disclosure to provide an individually packaged product that can be placed in a bag, pocket or the like and easily carried, since the absorbent article is poorly visible through the outer surface of the individually packaged product, and color transfer does not easily take place with other individually packaged products.

Solution to Problems

As a result of diligent research directed toward solving the problems described above, the present inventors have found an individually packaged product having an absorbent article which has an adhesive section on a non-skin-contacting surface thereof, and which is wrapped with a packaging sheet, wherein the individually packaged product is formed by anchoring the absorbent article on an inner surface of the packaging sheet sandwiching the adhesive section, while folding the packaging sheet with the absorbent article on the inner surface, the packaging sheet has a releasable colored section on the inner surface, the colored section is visible through an outer surface of the individually packaged product but the absorbent article is not visible through the outer surface of the individually packaged product.

Advantageous Effects of Invention

The individually packaged product of the present disclosure can be placed in a bag, pocket or the like and easily carried, since the absorbent article is poorly visible through the outer surface of the individually packaged product, and color transfer does not easily take place with other individually packaged products.

DESCRIPTION OF EMBODIMENTS

The individually packaged product of the present disclosure will now be explained in detail.

Figure 1:
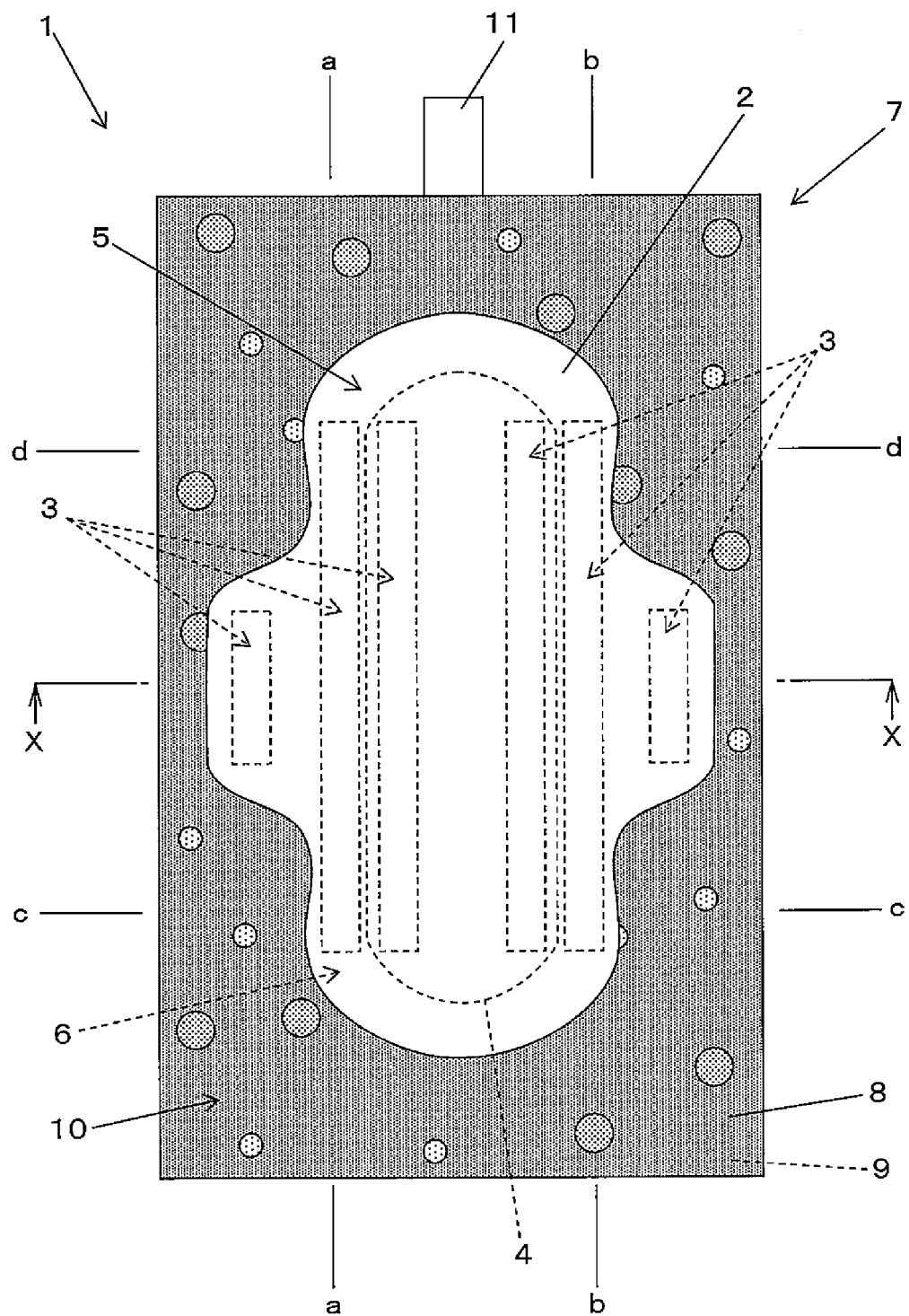
FIG. 1 is an expanded view of an embodiment of the individually packaged product of the present disclosure.

FIG. 1 is an expanded view of an embodiment of the individually packaged product of the present disclosure, as observed from the absorbent article side.

The individually packaged product 1 shown in FIG. 1 comprises an absorbent article 2 as a sanitary napkin, a packaging sheet 7 packaging the absorbent article 2, and a tab 11. The absorbent article 2 has an absorbent body 4 and an adhesive section 3 on the non-skin-contacting surface 6. The individually packaged product 1 is formed by anchoring the absorbent article 2 to the inner surface 8 of the packaging sheet 7, sandwiching the adhesive section 3, and folding the packaging sheet 7 with the absorbent article 2 on the inner surface.

The individually packaged product 1 shown in FIG. 1 has a total of six adhesive sections 3 extending in the lengthwise direction of the absorbent article 2, two overlapping with the absorbent body 4, two on the hem part of the body of the absorbent article 2 except for the side flaps, and two disposed on the side flaps of the absorbent article 2.

The location of the adhesive section is an example, and according to a different embodiment of the individually packaged product of the present disclosure, the location of the adhesive section is not particularly restricted so long as the absorbent article is anchored to the underwear of the user.

The packaging sheet 7 has a releasable first colored section 10 on the inner surface 8. The skin-contacting surface 5 of the absorbent article and the outer surface 9 of the packaging sheet 7 are shown in FIG. 1.

Throughout the present specification, the phrase "colored section on the inner surface of the packaging sheet" may be referred to as "first colored section" to differentiate it from the other colored sections.

Also, the denotations a-a, b-b, c-c and d-d in FIG. 1 are the folding lines of the individually packaged product 1.

In the attached drawings, the density of the dots in the first colored section 10 of the packaging sheet 7, and in the second colored section and third colored section described hereunder, indicate the color density.

Figure 2:
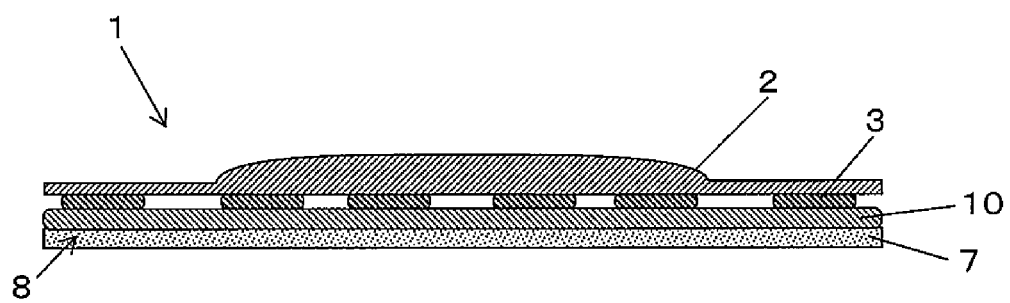
FIG. 2 is a cross-sectional view of the individually packaged product 1 in FIG. 1, along X-X.

FIG. 2 is a cross-sectional view of the individually packaged product 1 in FIG. 1, along X-X. In the individually packaged product 1 shown in FIG. 2, the absorbent article 2 is anchored to the inner surface 8 of the packaging sheet 7, sandwiching the adhesive section 3. In the individually packaged product 1 shown in FIG. 2, the detachment force is 2.6N or less when the absorbent article 2 is detached from the packaging sheet 7 along the lengthwise direction of the absorbent article 2.

Figure 3:
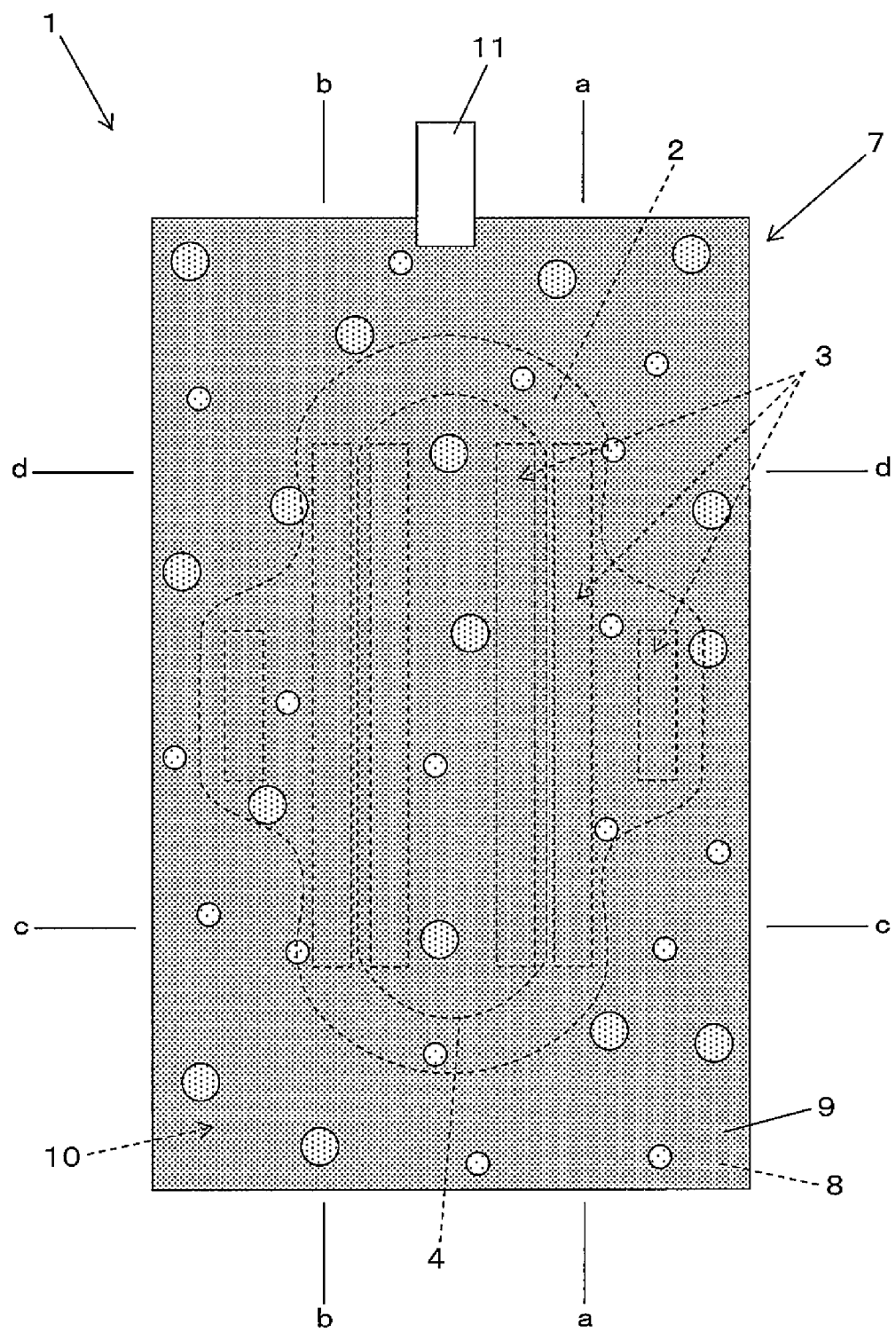
FIG. 3 is an expanded view of the individually packaged product 1 shown in FIG. 1, as observed from the outer surface of the packaging sheet.

FIG. 3 is an expanded view of the individually packaged product shown in FIG. 1, as observed from the outer surface of the packaging sheet. In FIG. 3, the packaging sheet 7 has no colored section on the outer surface 9, and the first colored section 10 is visible from the outer surface through the packaging sheet 7, while the absorbent article 2 is not visible from the outer surface.

Throughout the present specification, "the absorbent article is not visible through the outer surface of the individually packaged product" means that when the individually packaged product of the present disclosure is casually observed, it is not obvious that an absorbent article is contained in the individually packaged product. Since it is assumed that the individually packaged product of the present disclosure is to be placed in a bag, pocket or the like and simply carried, it is essential that other persons cannot discern that an absorbent article is contained in the individually packaged product when it is casually removed from the bag or pocket or when the contents of the bag are viewed under such conditions.

Thus, cases where it can be discerned that an absorbent article is contained in the individually packaged product by close observation of the individually packaged product of the present disclosure, for example, the absorbent article contained in the individually packaged product is visible through thin sections of the pattern, or an absorbent article-like object is discernible through the opening of the individual package, are not included in the description "visible".

In order to render the absorbent article not visible through the outer surface of the individually packaged product, the packaging sheet may have a first colored section over the entire inner surface, for example.

Also, in order to render the absorbent article not visible through the outer surface of the individually packaged product, the visible light transmittance of the packaging sheet with the first colored section and the optional second colored section is preferably about 75% or less, more preferably about 65% or less and even more preferably about 60% or less. If the transmittance exceeds about 75%, the absorbent article may sometimes be visible through the outer surface of the individually packaged product.

The lower limit for the visible light transmittance is about 0%. For example, an embodiment in which the visible light transmittance of the packaging sheet material itself is high but the masking property of the first colored section is high, resulting in a visible light transmittance of 0%, has the colored section visible through the outer surface of the individually packaged product, but since the absorbent article is not visible through the outer surface of the individually packaged product, such a mode is included according to one embodiment of the individually packaged product of the present disclosure.

The present inventors have found that if the detachment force during detachment of the absorbent article from the packaging sheet along the lengthwise direction of the absorbent article is limited to a certain value or less, the user feels that the absorbent article is easier to detach when the individually packaged product is opened and the absorbent article is detached from the packaging sheet. The detachment force along the lengthwise direction of the absorbent article is used because an absorbent article is usually detached from the packaging sheet along the lengthwise direction. According to one embodiment of the individually packaged product of the present disclosure, the detachment force is about 2.6N or less, preferably about 2.3N or less and more preferably about 2.0N or less. If the detachment force is greater than about 2.6N, the user will tend to feel that it is difficult to detach the absorbent article from the packaging sheet and that it becomes stuck during detachment.

The detachment force is a value determined by factors such as the adhesion of the adhesive section, the release property of the colored section (work of adhesion, etc.) and the amount of the adhesive section (the length of the adhesive section in the widthwise direction of the absorbent article), but if the detachment force that includes all of these factors is about 2.6N or less, the user feels that the absorbent article is easy to detach from the packaging sheet.

The detachment force is particularly important when the colored section of the individually packaged product is formed by gravure printing as described below. In gravure printing, a simple colored material is used for printing while varying the amount per unit area, to form a predetermined pattern, i.e. colored gradations, but since the sparse color sections have a low amount of colored material per unit area, that is, they have a low amount of detachable component per unit area, they tend to have an inferior detachment property compared to the dense color sections (i.e., the sections with large amounts of detachable component).

The unit area is the unit area of the packaging sheet.

There is no particular lower limit for the value of the detachment force, but when it is preferred for the absorbent article to be anchored to the packaging sheet, such as when it is not desirable for the absorbent article to move inside the individually packaged product when it is carried, or when it is desired to prevent the absorbent article from falling off when the user holds the packaging sheet during exchange, the detachment force may be above a certain value, such as about 0.5N or greater, about 0.7N or greater or about 1.0N or greater.

The detachment force is measured in the following manner.

(1) A TENSILON-type constant-extension tensile tester is prepared.

(2) The lengthwise ends of the absorbent article are set on a jig so that the center of the absorbent article in the widthwise direction is anchored, while the lengthwise ends of the packaging sheet are set on another jig so that the center of the packaging sheet in the widthwise direction is anchored. The jigs used may be ones with a width of 30 mm, for example.

(3) A tensile test is conducted with a jig spacing of 20 mm and a pull rate of 500 mm/min, until the absorbent article and the packaging sheet are completely separated.

(4) In the tensile test, the maximum tensile force is recorded, as the maximum value for the tensile force.

(5) The tensile test is repeated 20 times for different individually packaged products, and the maximum value of the data for the total of 20 maximum tensile forces is recorded as the detachment force (N).

The reason for stipulating the detachment force in this manner is as follows.

The ease of detachment when the absorbent article is detached from the packaging sheet is determined by the relative positional relationship between the adhesive section of the absorbent article and the first colored section of the packaging sheet, for example, the relative positional relationship between the adhesive section of the absorbent article and the pattern of the first colored section of the packaging sheet, and their specific positional relationship may differ for each individually packaged product. For example, when the first colored section is formed by gravure printing, a larger area of the adhesive section contacting with the sparse color sections of the first colored section will result in a larger maximum tensile force.

Thus, since some variation occurs in the ease of detachment when detaching the absorbent article from the packaging sheet, it may be necessary to evaluate the maximum tensile force for a certain range of individually packaged products.

Moreover, upon further detachment, i.e. a widening jig spacing, in this tensile test, the value of the tensile force undergoes tiny fluctuations, and generally a tensile force chart with numerous peaks and numerous bottoms is obtained. According to one embodiment of the individually packaged product of the present disclosure, the peak average value, which is the average value for the tensile force at multiple peaks, is about 1.2N or less, and preferably about 1.1N or less. If the peak average value is about 1.2N or less, it will be possible to accomplish smooth detachment without sticking, when the absorbent article is detached from the packaging sheet.

Figure 4:
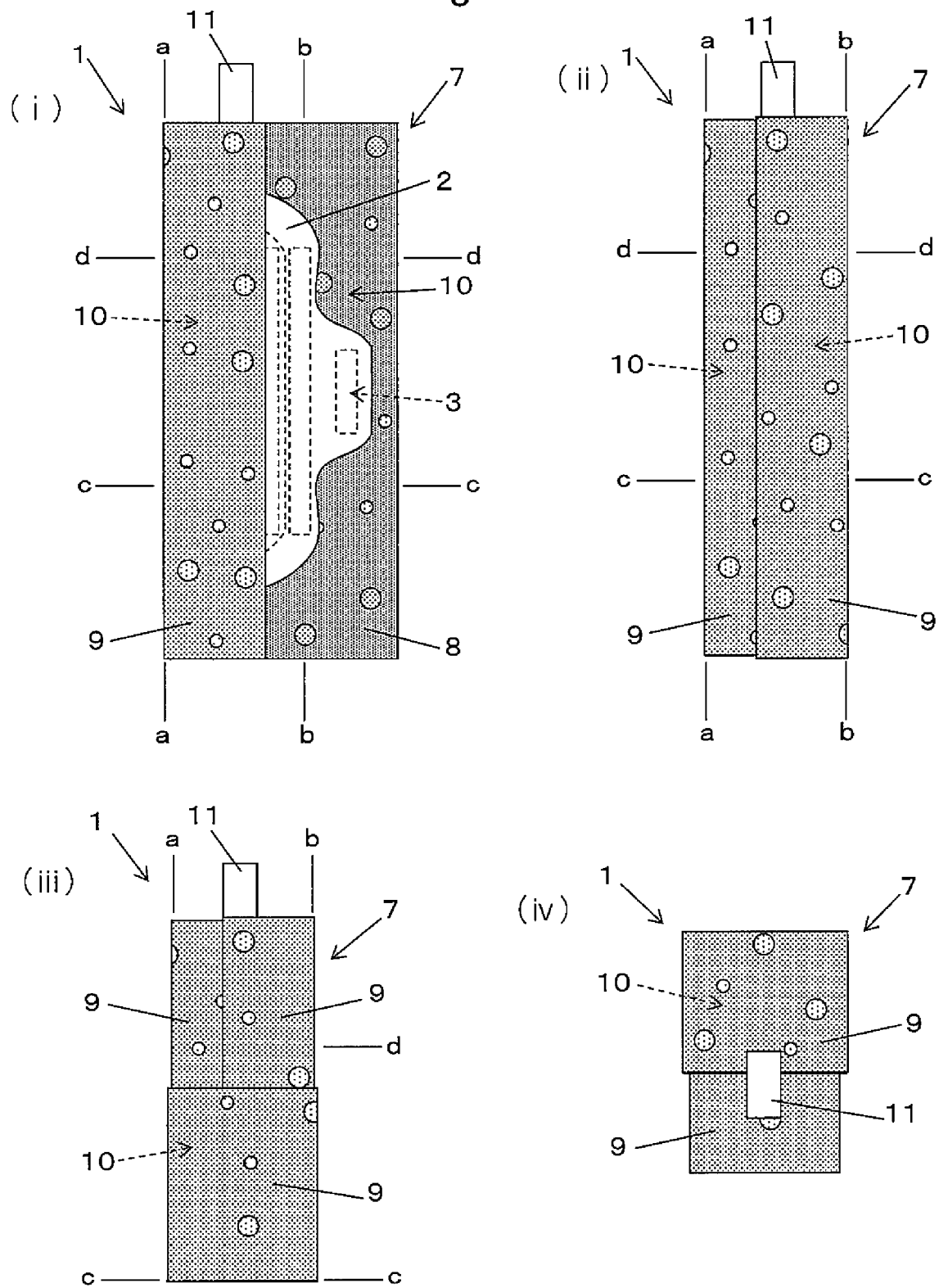
FIG. 4 is a drawing illustrating a folded structure for the individually packaged product shown in FIG. 1 to FIG. 3.

FIG. 4 is a drawing illustrating a folded structure for the individually packaged products shown in FIG. 1 to FIG. 3. The individually packaged product 1 shown in FIG. 4 is formed by being folded over four times along two folding lines (a-a and b-b) parallel with the lengthwise direction of the absorbent article 2, and two folding lines (c-c and d-d) perpendicular to the lengthwise direction.

More specifically, in the individually packaged product 1 shown in FIG. 4, the absorbent article 2 and packaging sheet 7 are first folded along folding line a-a, as shown in FIG. 4(*i*), with the left-hand region of the absorbent article 2 and packaging sheet 7 left of the folding line a-a, being folded onto the region defined by folding line a-a and folding line b-b.

In the left-hand region, the first colored section 10 can be seen through the packaging sheet 7.

Next, as shown in FIG. 4(*ii*), the right-hand region of the absorbent article 2 and packaging sheet 7 right of the folding line b-b is folded along folding line b-b over the outer surface 9 of the packaging sheet 7 in the left-hand region, in the middle region.

In the left-hand region and right-hand region, the first colored section 10 can be seen through the packaging sheet 7.

Similarly, as shown in FIG. 4(*iii*), the lower region at the lower end of the absorbent article 2 and packaging sheet 7 is folded along the folding line c-c, onto the middle region defined by folding line c-c and folding line d-d, and then as shown in FIG. 4(*iv*), the upper region at the upper end of the absorbent article 2 and packaging sheet 7 is folded along the folding line d-d onto the middle region, and is fixed with a tab 11, thereby forming an individually packaged product 1.

In the individually packaged product 1 illustrated in FIG. 4(*iv*), the first colored section 10 is entirely visible through the packaging sheet 7.

According to another embodiment of the individually packaged product of the present disclosure, the folded structure may be appropriately fixed using a tab, hot-melt adhesive or the like.

As shown in FIG. 4(*iv*), the first colored section is visible through the outer surface of the individually packaged product, while the absorbent article is not visible through the outer surface of the individually packaged product.

In the embodiments illustrated in FIGS. 1 to 4, the first colored section is formed over the entire inner surface of the packaging sheet, but according to another embodiment of the individually packaged product of the present disclosure, the first colored section does not necessarily need to be formed over the entire inner surface of the packaging sheet, so long as the absorbent article is not visible through the outer surface. For example, in the packaging sheet, the first colored section may be formed only in the region that is externally visible in the individually packaged product, such as the region defined by folding line a-a and folding line b-b, or the region defined by folding line c-c and folding line d-d, in FIG. 3.

In FIGS. 1 to 4, the absorbent article 2 is anchored onto the inner surface 8 of the packaging sheet 7 sandwiching the adhesive section 3, and if the absorbent article is anchored to the inner surface of the packaging sheet as shown in FIGS. 1 to 4, the absorbent article inside the individually packaged product moves minimally in directions different from the packaging sheet, i.e. the absorbent article undergoes little friction with the first colored section on the inner surface of the packaging sheet, and hence the color shade of the first colored section does not easily transfer onto the inner surface of the packaging sheet to the absorbent article.

In FIGS. 1 to 4, the individually packaged product 1 is formed by folding the absorbent article 2 and packaging sheet 7 four times, but according to a different embodiment of the individually packaged product of the present disclosure, the absorbent article and/or packaging sheet do not need to be folded, or even if the absorbent article and/or packaging sheet are folded, there is no particular restriction on the number of folds.

Figure 5:
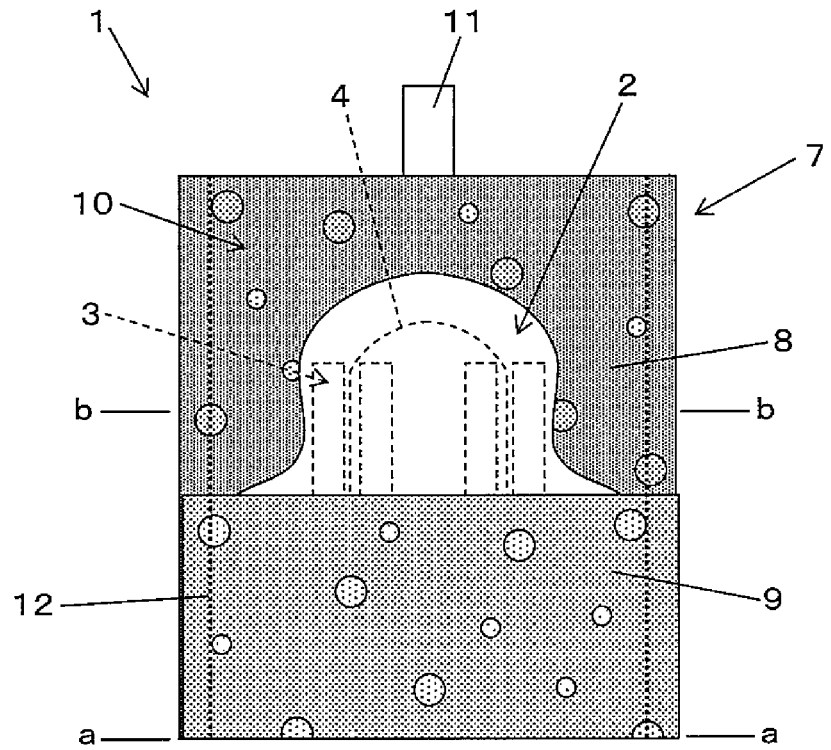
FIG. 5 is a drawing illustrating an example of a triple-fold individually packaged product.

FIG. 5 is a drawing illustrating an example of a triple-fold individually packaged product, as an embodiment of the individually packaged product of the present disclosure. The individually packaged product 1 shown in FIG. 5 comprises an absorbent article 2 as a sanitary napkin, a packaging sheet 7 packaging the absorbent article 2, and a tab 11. The absorbent article 2 has an absorbent body 4 and an adhesive section 3 on the non-skin-contacting surface. The individually packaged product 1 shown in FIG. 5 is formed by folding the absorbent article 2 and packaging sheet 7 at folding line a-a and folding line b-b, which are two folding lines perpendicular to the lengthwise direction, and by sealing the sides in the lengthwise direction at the heat seal 12, but in FIG. 5 it is shown with the tab 11 raised and the folding line b-b opened, for ease of explanation.

According to one embodiment of the individually packaged product of the present disclosure, the first colored section also has a detaching property which allows the absorbent article to be easily detached from the packaging sheet. A first colored section having such a detaching property is formed by coating the packaging sheet with a colored material comprising a coloring component, a detachable component, and optionally a base resin such as acryl or polyester.

The coloring component may be a pigment and/or dye, but is preferably a pigment in order to avoid color transfer caused by water wetting, and the pigment may be, for example, an inorganic pigment such as cobalt oxide, titanium dioxide, titanium black or titanium yellow, an organic pigment such as an azo-based pigment or phthalocyanine-based pigment, or a fluorescent pigment composed mainly of an oxide, sulfide, silicide, phosphate or tungstate of calcium, barium, magnesium, cadmium or the like.

The amount of the coloring component for exhibiting the effect of the present disclosure will vary depending on the type, amount and size of the coloring component, and also depending on the colored section on the outer surface of the packaging sheet, described hereunder, but the coloring component is preferably present at about 1 to about 30 mass %, more preferably about 2 to about 20 mass % and even more preferably about 3 to about 10 mass % in the first colored section, based on the total mass of the first colored section.

The colored material is preferably a curable material comprising a crosslinkable functional group, such as a thermosetting or radiation-curing material, for example, a UV curable material, so that the first colored section to be formed does not transfer its color to the absorbent article. Considering that the packaging sheet in which the first colored section is to be formed will usually be a sheet with a low melting point and/or glass transition temperature, the colored material is preferably a radiation-curing material, such as a UV curable material, which does not deform the packaging sheet.

The detachable component may be a silicone resin, fluorine resin, octadecyl isocyanate, or the like.

As mentioned above, if the first colored section has a detaching property, this has advantages such as lowering of production cost, since there is no need to separately provide the detaching portion and release sheet described below, increase in the production rate since there is no need to position the pressure-sensitive adhesive section and the detaching region, and reduction of waste, since there is no need for a release sheet.

The first colored section is not particularly restricted so long as the first colored section is visible through the outer surface of the individually packaged product while the absorbent article is not visible through the outer surface of the individually packaged product, and for example, it may have a single color such as pink or sea-blue, or the first colored section may have a pattern.

The method for forming the first colored section on the inner surface of the packaging sheet is not particularly restricted, and for example, and when a first colored section with a single color is to be formed, the first colored section may be formed by coating the packaging sheet with the colored material using means such as roll coating or spray coating.

The first colored section may also be formed on the inner surface of the packaging sheet by means such as printing. Gravure printing, for example, may be used to coat the packaging sheet with a single colored material while varying the amount per unit area, to form a first colored section having a predetermined pattern. Means such as gravure printing is advantageous from the viewpoint of production cost, since it allows a pattern to be formed from a single colored material by varying the amount per unit area.

Alternatively, means such as screen printing or flexographic printing may be used to coat the packaging sheet with a plurality of colored materials with different color shades, to form a first colored section having a predetermined pattern.

In the individually packaged product of the present disclosure, the packaging sheet has a first colored section on the inner surface, the first colored section being visible through the outer surface of the individually packaged product, and the absorbent article being not visible through the outer surface of the individually packaged product. In order for the first colored section to have this function, the first colored section must have a consistent masking property that conceals the absorbent article inside it. The masking property is mainly determined by the type, amount and size of the coloring components such as the pigment and/or dye in the first colored section, and generally a consistent masking property is obtained by including the coloring component in the amount specified above.

In the embodiments illustrated in FIGS. 1 to 5, the packaging sheet does not have a colored section on the outer surface on the side opposite the inner surface, but according to another embodiment of the individually packaged product of the present disclosure, the packaging sheet may have a colored section on the outer surface.

Throughout the present specification, the phrase "colored section on the outer surface of the packaging sheet" may be referred to as "second colored section" to differentiate it from the other colored sections.

Figure 6:
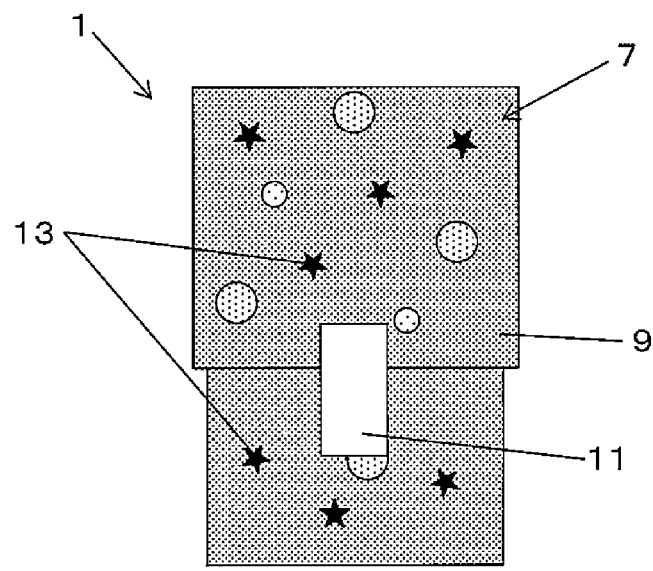
FIG. 6 is a drawing illustrating an example of an individually packaged product according to one embodiment of the individually packaged product of the present disclosure, having a second colored section on the outer surface of the packaging sheet.

FIG. 6 is a drawing illustrating an example of an individually packaged product according to one embodiment of the individually packaged product of the present disclosure, having a second colored section on the outer surface of the packaging sheet.

The individually packaged product 1 shown in FIG. 6 is formed by being folded a total of four times and anchoring with a tab 11, as shown in FIG. 4, and the packaging sheet 7 has a second colored section 13 comprising a plurality of star shapes, arranged in a random manner on the outer surface 9.

The first colored section and second colored section may have the same pattern, or the first colored section and second colored section may have different patterns, as shown in FIG. 6. In order to reduce the feeling of melancholy during menstrual periods, the pattern of the first colored section and the pattern of the second colored section may be different.

Also, if the second colored section is a small pattern with lower subjective brightness, i.e. with dense coloring, the visual line of an observer can be led to the second colored section, so that the absorbent article in the individually packaged product is not recognized.

The second colored section on the outer surface of the packaging sheet preferably has a smaller area than the area of the first colored section on the inner surface of the packaging sheet.

This is because if the area of the second colored section is increased, problems such as color transfer, where color shades of the colored material become transferred to adjacent objects, can occur due to abrasion in the manufacturing line during production, abrasion between individually packaged products during distribution, or abrasion inside the bag after purchase. Furthermore, in order to avoid impairing the design property of the individually packaged product, the second colored section preferably has a smaller area than the area of the first colored section.

Although the absorbent article does not have a colored section in each of the individually packaged products shown in FIGS. 1 to 6, according to a different embodiment of the individually packaged product of the present disclosure, the absorbent article may also have a colored section on the outer surface of the packaging sheet side, and the packaging sheet may have the first colored section and optionally a second colored section in such a manner that the colored section on the outer surface of the absorbent article is not visible through the outer surface of the individually packaged product.

Throughout the present specification, the phrase "colored section on the outer surface of the absorbent article" may be referred to as "third colored section" to differentiate it from the other colored sections.

Figure 7:
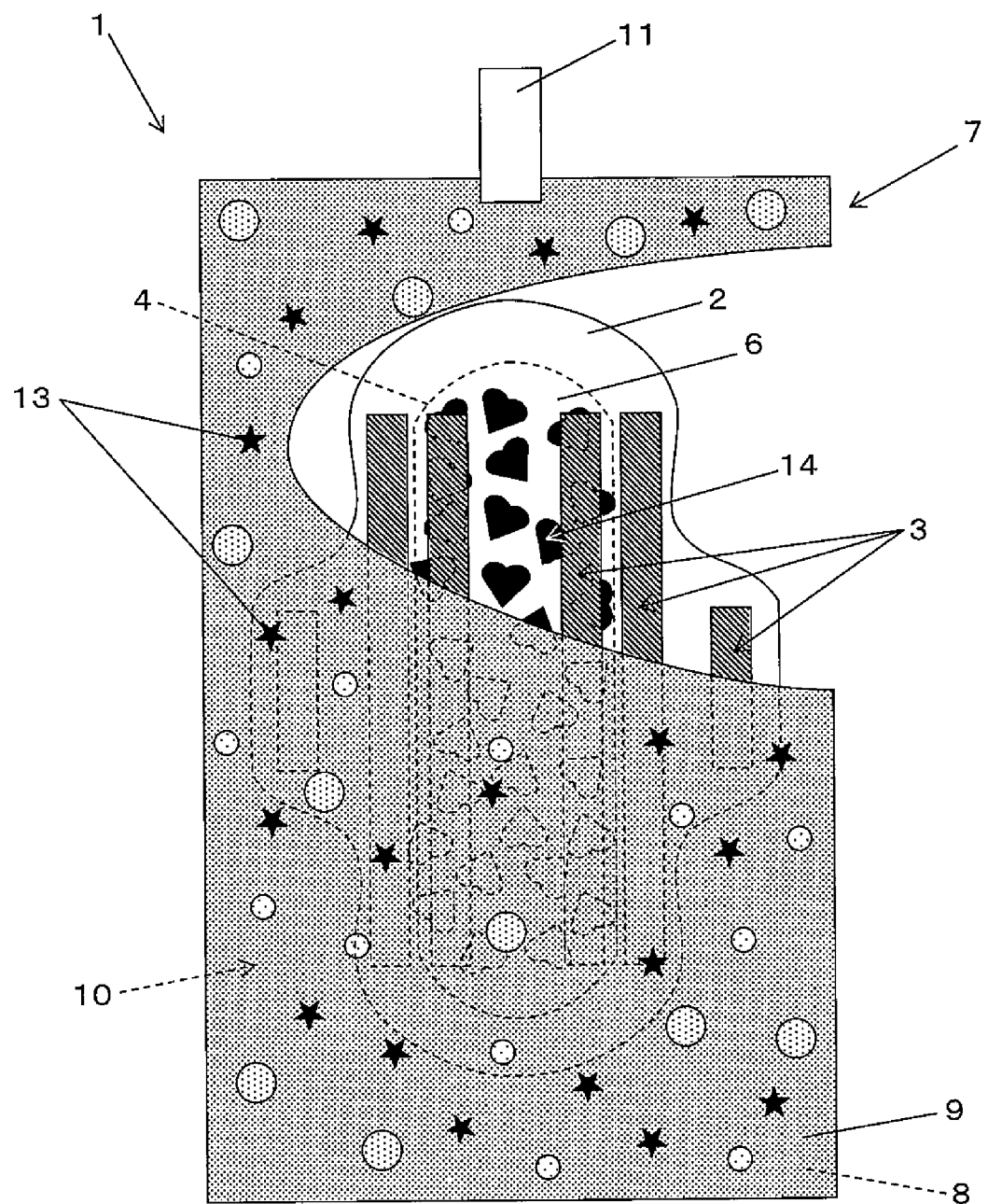
FIG. 7 is an expanded view of an embodiment of the individually packaged product of the present disclosure, being an embodiment having a colored section on the outer surface of the absorbent article.

FIG. 7 is an expanded view of an embodiment of the individually packaged product of the present disclosure, being an embodiment having a colored section on the outer surface of the absorbent article.

The individually packaged product 1 shown in FIG. 7 comprises an absorbent article 2 as a sanitary napkin, a packaging sheet 7 packaging the absorbent article 2, and a tab 11. The absorbent article 2 has an absorbent body 4 and an adhesive section 3 on the non-skin-contacting surface 6, there being formed on the non-skin-contacting surface 6 of the absorbent article 2 a third colored section 14 composed of a predetermined pattern. Also, in the individually packaged product 1 shown in FIG. 8, the packaging sheet 7 has the first colored section 10 on the inner surface 8, and has the second colored section 13 with a plurality of dots arranged in a square zigzag fashion, on the outer surface 9.

In the individually packaged product 1 shown in FIG. 7, the absorbent article 2 is anchored to the inner surface 8 of the packaging sheet 7, sandwiching the adhesive section 3, while the absorbent article 2 and packaging sheet 7 are folded with the absorbent article 2 facing inward, thereby forming an individually packaged product 1.

The third colored section will usually be attached to the non-skin-contacting surface of the back sheet of a sanitary napkin or a winged reinforcing sheet, in order to reduce the feeling of melancholy during the menstrual period of the user. However, since awareness of the menstrual period may be emphasized when the third colored section can be seen through the outer surface of the individually packaged product before use, the third colored section is preferably not visible through the outer surface of the individually packaged product.

In order for the packaging sheet to have the first colored section and optionally the second colored section in such a manner that the colored section on the outer surface of the absorbent article is not visible through the outer surface of the individually packaged product, for example:

(i) the masking property of the first colored section and/or second colored section may be increased to physically block visibility of the third colored section through the exterior, (ii) the color shade of the first colored section and/or second colored section may be similar to the color shade of the third colored section to render the third colored section less apparent through the exterior, or (iii) the chroma of the third colored section may be reduced to render the third colored section less apparent through the exterior.

The second colored section and third colored section may have the same composition as the first colored section and may be formed by the same method as the first colored section, but the detachable component it not essential.

The absorbent article to be used for some embodiments of the individually packaged product of the present disclosure is not particularly restricted so long as it is one that is to be sold as an individual package and can be used by attachment to, for example, the underwear of a user, and a sanitary napkin or panty liner may be mentioned as an example.

The packaging sheet to be used for some embodiments of the individually packaged product of the present disclosure is also not particularly restricted so long as it is one used in the technical field for individual packaging of absorbent articles, and examples include woven fabrics, nonwoven fabrics, felt, pile, films, sheets and laminates of the foregoing.

A coloring component such as a pigment or dye may be added to the packaging sheet to alter the visible light transmittance and color shade of the packaging sheet. By altering the visible light transmittance and color shade of the packaging sheet, it is possible to change the appearance of the color shade and pattern of the first colored section before and after the individually packaged product is opened, and to reduce melancholy during the menstrual period.

The adhesive section used for certain embodiments of the individually packaged product of the present disclosure may employ an adhesive commonly used in the technical field, such as a hot-melt pressure-sensitive adhesive, which may be a polyolefinic (for example, polyethylene or polypropylene) hot-melt pressure-sensitive adhesive, an ethylene/vinyl acetate copolymer-based hot-melt pressure-sensitive adhesive, synthetic rubber-based (for example, styrene-based copolymer, butadiene-based copolymer or isoprene-based copolymer) hot-melt pressure-sensitive adhesive, an acrylic resin-based pressure-sensitive adhesive, or a polyvinyl alcohol-based pressure-sensitive adhesive.

EXAMPLES

The present disclosure will now be explained in fuller detail by examples, with the understanding that it is not meant to be limited to the examples.

Example 1

Pink, blue and yellow colored materials were coated onto a polyethylene film using a gravure printer, varying the cell sizes, to form packaging sheets No. 1 to 12. The transmittances of packaging sheets No. 1 to 12 were then measured.

The transmittances were measured using an A300/ZE-2000 flicker photometric color difference meter by Nippon Denshoku Industries Co., Ltd.

The same packaging sheet was measured 5 times at different locations, and the average value was recorded as the measured value. The results are shown in Table 1.

Example 2

A commercially available sanitary napkin was attached to each of packaging sheets Nos. 1 to 12 with a pressure-sensitive adhesive, and the sanitary article was folded inward as shown in FIG. 3 to form an individually packaged product. Each individually packaged product was casually observed by ten participants, and it was judged whether or not the sanitary napkin in the individually packaged product was visible. The results are summarized in Table 1. A value of 10% visibility means that one participant judged the sanitary napkin in the individually packaged product to be visible.

Example 3

Eight different commercially available individual packaged sanitary napkins (commercial products A-H) were acquired, and the transmittances of the packaging sheets (Nos. 13 to 20) were measured in the same manner as Example 1. The results are shown in Table 1.

The packaging sheets of commercially available individually packaged sanitary napkins are either provided with colored sections on the outer surfaces of the packaging sheets, or the packaging sheets themselves are colored, or combinations of these methods are used. None of the commercially available individually packaged sanitary napkins had a colored section provided on the inner surface of the packaging sheet.

Example 4

In packaging sheets Nos. 13 to 20, the same type of absorbent article used in Example 2 is attached with a pressure-sensitive adhesive, and the visibility was evaluated in the same manner as Example 2. The results are summarized in Table 1.

TABLE 1

| No. | Color | Transmittance (%) | Visibility |
|---|---|---|---|
| 1 | Pink | 56.9 | 0% |
| 2 | Pink | 52.4 | 0% |
| 3 | Pink | 48.9 | 0% |
| 4 | Pink | 45.0 | 0% |
| 5 | Yellow | 60.5 | 0% |
| 6 | Yellow | 59.0 | 0% |
| 7 | Yellow | 57.1 | 0% |
| 8 | Yellow | 53.7 | 0% |
| 9 | Blue | 56.7 | 0% |
| 10 | Blue | 53.3 | 0% |
| 11 | Blue | 45.6 | 0% |
| 12 | Blue | 43.9 | 0% |
| 13 | White (Commercial product A) | 74.5 | 20% |
| 14 | Yellow (Commercial product B) | 54.8 | 0% |
| 15 | Green (Commercial product C) | 54.7 | 0% |
| 16 | Pink (Commercial product D) | 54.6 | 0% |
| 17 | Blue (Commercial product E) | 54.3 | 0% |
| 18 | Orange (Commercial product F) | 50.2 | 0% |
| 19 | Pink (Commercial product G) | 34.7 | 0% |
| 20 | Blue (Commercial product H) | 31.2 | 0% |

With a transmittance of about 75%, 80% of the participants responded that the absorbent article was not visible through the outer surface of the individually packaged product, whereas with a transmittance of up to 60%, 100% of the participants responded that the absorbent article was not visible through the outer surface of the individually packaged product, regardless of the color of the colored section.

Example 5

Detachment Force and Peak Average Value

Figure 8:
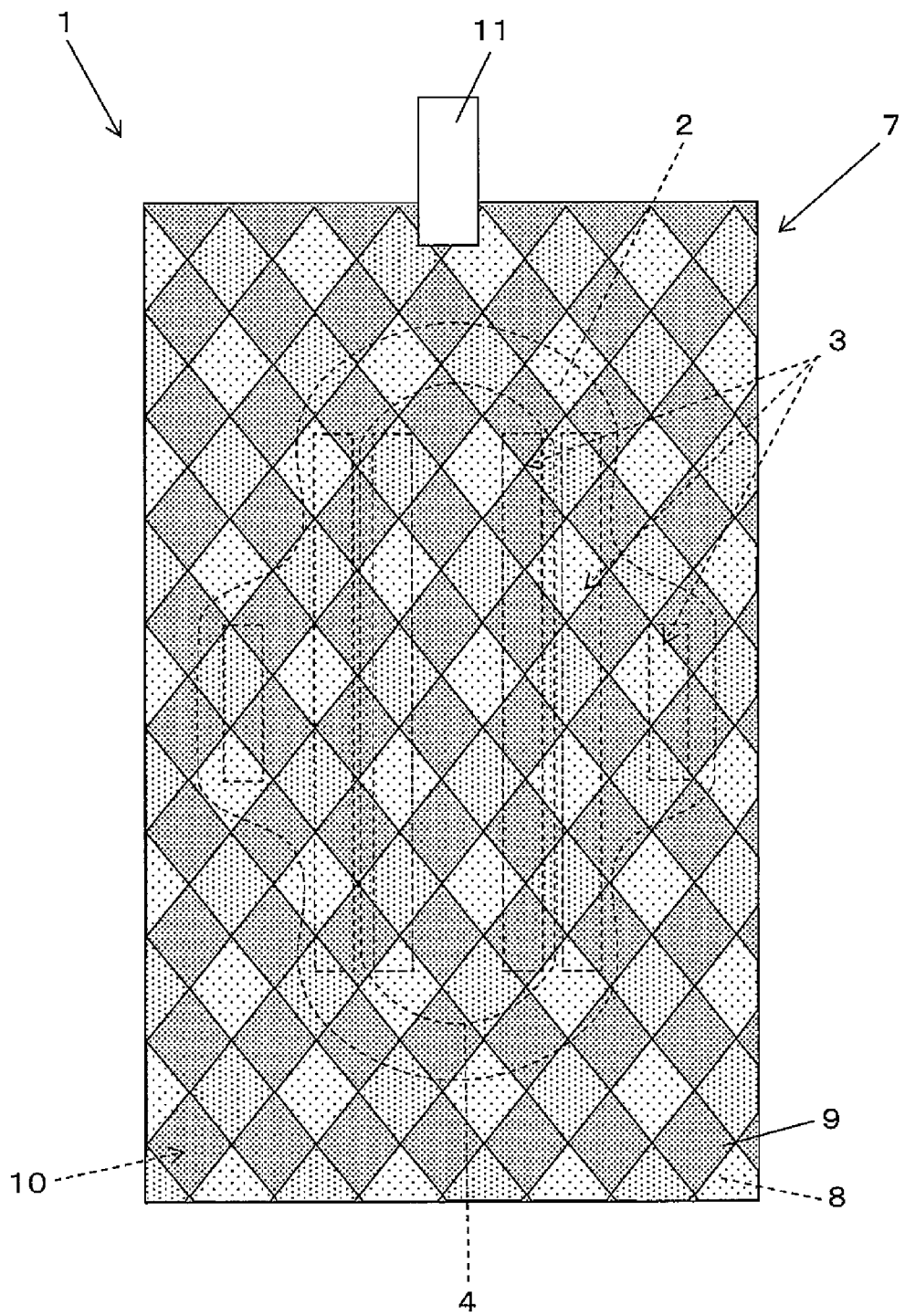
FIG. 8 is an expanded view of an individually packaged product having a lattice pattern used in Example 5, as observed from the outer surface of the packaging sheet.

There were prepared an individually packaged product having a colored section with a polka dot pattern on the inner surface of the packaging sheet (hereunder referred to as "polka dot-patterned individually packaged product"), as shown in FIG. 3, and an individually packaged product having a colored section with a lattice-like pattern on the inner surface of the packaging sheet (hereunder referred to as "lattice-patterned individually packaged product"), as shown in FIG. 8. The colored sections of the polka dot-patterned individually packaged product and the lattice-patterned individually packaged product were both formed by gravure printing, and the sections other than the colored sections were identical.

That is, the individually packaged products 1 shown in FIG. 3 and FIG. 8 comprise an absorbent article 2 as a sanitary napkin, a packaging sheet 7 packaging the absorbent article 2, and a tab 11. The absorbent article 2 has an absorbent body 4 and an adhesive section 3 on the non-skin-contacting surface, and the packaging sheet 7 has a detachable first colored section 10 on the inner surface 8. The individually packaged products 1 shown in FIG. 3 and FIG. 8 have a total of six adhesive sections 3 extending in the lengthwise direction of the absorbent article 2, two overlapping with the absorbent body 4, two on the hem part of the body of the absorbent article 2 except for the side flaps, and two disposed on the side flaps of the absorbent article 2.

In the polka dot-patterned individually packaged product shown in FIG. 3 there was no sparsely colored section in the region of the first colored section 10 contacting with the adhesive section 3, but in the lattice-patterned individually packaged product shown in FIG. 8, a sparsely colored section was present in the region of the first colored section 10 contacting with the adhesive section.

The polka dot-patterned individually packaged product and the lattice-patterned individually packaged product were evaluated for detachment force and peak average value, by the methods described herein. The results are shown in Table 2 below.

TABLE 2

|  | Peel force (N) | Peak average value (N) |
|---|---|---|
| Polka dot patterned individually packaged product | 1.83 | 1.03 |
| Lattice-patterned individually packaged product | 2.88 | 1.27 |

Table 2 shows that if there is no sparsely colored section, i.e. no section with low detachable component, in the region of the first colored section contacting with the adhesive section, then the detachment force and the peak average value are small.

Example 6

Contact Angle

The relationship between the plate control and work of adhesion in gravure printing was evaluated.

A FACE Model CA-V contact angle meter by Kyowa Interface Science Co., Ltd. was used to calculate the work of adhesion from the water contact angle. The work of adhesion (W) is calculated by the following formula (1):

$$W = 72.75 \times (1 + \cos \theta)$$

where the water contact angle is θ, based on the Young-Dupre equation with a water surface tension of 72.75 mN/m.

The measurement was conducted at 20° C., and the average value of five measurements was recorded as the measured value.

The results are summarized in Table 3 below. For comparison, the work of adhesion was also measured for a packaging sheet and a common release sheet.

TABLE 3

|  | Plate control 70% | Plate control 50% | Plate control 30% | Plate control 20% | Packaging sheet | Release sheet |
|---|---|---|---|---|---|---|
| Contact angle (°) | 104.9 | 103.8 | 103.5 | 100.3 | 69.7 | 107.9 |
| W (mN/m) | 54.1 | 55.3 | 55.7 | 59.8 | 98.0 | 50.3 |

Table 3 suggests that a smaller plate control results in a lower amount of colored material and detachable component per unit area, and in some cases partial sections are produced in the packaging sheet that are not coated by colored sections, resulting in increased work of adhesion and resistance to detachment.

Specifically, the present disclosure relates to the following J1 to J6.

[J1]
An individually packaged product having an absorbent article which has an adhesive section on a non-skin-contacting surface thereof, and which is wrapped with a packaging sheet,
wherein the individually packaged product is formed by anchoring the absorbent article on an inner surface of the packaging sheet sandwiching the adhesive section, while folding the packaging sheet with the absorbent article on the inner surface,
the packaging sheet has a releasable colored section on the inner surface, the colored section is visible through an outer surface of the individually packaged product but the absorbent article is not visible through the outer surface of the individually packaged product.

[J2]
The individually packaged product according to J1, wherein a detachment force is 2.6N or less when the absorbent article is detached from the packaging sheet along a lengthwise direction of the absorbent article.

[J3]
The individually packaged product according to J1 or J2, wherein the colored section on the inner surface of the packaging sheet is formed by coating the inner surface of the packaging sheet with a simple colored material while varying an amount per unit area, and the colored section on the inner surface of the packaging sheet forms a predetermined pattern on the inner surface of the packaging sheet.

[J4]
The individually packaged product according to any one of J1 to J3, wherein the packaging sheet has the colored section over the entire inner surface on the absorbent article side.

[J5]
The individually packaged product according to any one of J1 to J4, wherein the packaging sheet further has a colored section on an outer surface on the side opposite the inner surface.

[J6]
The individually packaged product according to J5, wherein the absorbent article further has a colored section on an outer surface of the absorbent article, on the packaging sheet side, and the packaging sheet has the colored section on the inner surface of the packaging sheet and the colored section on the outer surface of the packaging sheet so that the colored section on the outer surface of the absorbent article is not visible through the outer surface of the individually packaged product.

REFERENCE SIGNS LIST

1 Individually packaged product
2 Absorbent article
3 Adhesive section
4 Absorbent body
5 Skin-contacting surface
6 Non-skin-contacting surface
7 Packaging sheet
8 Inner surface
9 Outer surface
10 First colored section
11 Tab
12 Heat seal
13 Second colored section
14 Third colored section

The invention claimed is:

1. An individually packaged product having an absorbent article which has an adhesive section on a non-skin-contacting surface thereof, and which is wrapped with a packaging sheet,
wherein the individually packaged product is formed by anchoring the absorbent article on an inner surface of the packaging sheet sandwiching the adhesive section, while folding the packaging sheet with the absorbent article on the inner surface,
the packaging sheet has a releasable colored section on the inner surface, the releasable colored section is visible through an outer surface of the individually packaged product but the absorbent article is not visible through any portion of the outer surface of the individually packaged product.

2. The individually packaged product according to claim 1, wherein a detachment force is 2.6N or less when the absorbent article is detached from the packaging sheet along a lengthwise direction of the absorbent article.

3. The individually packaged product according to claim 1, wherein the colored section on the inner surface of the packaging sheet is formed by coating the inner surface of the packaging sheet with a simple colored material while varying an amount per unit area, and the colored section on the inner surface of the packaging sheet forms a predetermined pattern on the inner surface of the packaging sheet.

4. The individually packaged product according to claim 1, wherein the packaging sheet has the colored section over the entire inner surface on the absorbent article side.

5. The individually packaged product according to claim 1, wherein the packaging sheet further has a colored section on an outer surface on the side opposite the inner surface.

6. The individually packaged product according to claim 5, wherein the absorbent article further has a colored section on an outer surface of the absorbent article, on the packaging sheet side, and the packaging sheet has the colored section on the inner surface of the packaging sheet and the colored section on the outer surface of the packaging sheet so that the colored section on the outer surface of the absorbent article is not visible through the outer surface of the individually packaged product.

7. The individually packaged product according to claim 2, wherein the colored section on the inner surface of the packaging sheet is formed by coating the inner surface of the packaging sheet with a simple colored material while varying an amount per unit area, and the colored section on the inner surface of the packaging sheet forms a predetermined pattern on the inner surface of the packaging sheet.

8. The individually packaged product according to claim 2, wherein the packaging sheet has the colored section over the entire inner surface on the absorbent article side.

9. The individually packaged product according to claim 3, wherein the packaging sheet has the colored section over the entire inner surface on the absorbent article side.

10. The individually packaged product according to claim 7, wherein the packaging sheet has the colored section over the entire inner surface on the absorbent article side.

11. The individually packaged product according to claim 2, wherein the packaging sheet further has a colored section on an outer surface on the side opposite the inner surface.

12. The individually packaged product according to claim 3, wherein the packaging sheet further has a colored section on an outer surface on the side opposite the inner surface.

13. The individually packaged product according to claim 7, wherein the packaging sheet further has a colored section on an outer surface on the side opposite the inner surface.

14. The individually packaged product according to claim 8, wherein the packaging sheet further has a colored section on an outer surface on the side opposite the inner surface.

15. The individually packaged product according to claim 9, wherein the packaging sheet further has a colored section on an outer surface on the side opposite the inner surface.

16. The individually packaged product according to claim 10, wherein the packaging sheet further has a colored section on an outer surface on the side opposite the inner surface.

17. The individually packaged product according to claim 11, wherein the absorbent article further has a colored section on an outer surface of the absorbent article, on the packaging sheet side, and the packaging sheet has the colored section on the inner surface of the packaging sheet and the colored section on the outer surface of the packaging sheet so that the colored section on the outer surface of the absorbent article is not visible through the outer surface of the individually packaged product.

18. The individually packaged product according to claim 12, wherein the absorbent article further has a colored section on an outer surface of the absorbent article, on the packaging sheet side, and the packaging sheet has the colored section on the inner surface of the packaging sheet and the colored section on the outer surface of the packaging sheet so that the colored section on the outer surface of the absorbent article is not visible through the outer surface of the individually packaged product.

19. The individually packaged product according to claim 13, wherein the absorbent article further has a colored section on an outer surface of the absorbent article, on the packaging sheet side, and the packaging sheet has the colored section on the inner surface of the packaging sheet and the colored section on the outer surface of the packaging sheet so that the colored section on the outer surface of the absorbent article is not visible through the outer surface of the individually packaged product.

20. The individually packaged product according to claim 14, wherein the absorbent article further has a colored section on an outer surface of the absorbent article, on the packaging sheet side, and the packaging sheet has the colored section on the inner surface of the packaging sheet and the colored section on the outer surface of the packaging sheet so that the colored section on the outer surface of the absorbent article is not visible through the outer surface of the individually packaged product.

\* \* \* \* \*